(12) United States Patent
Hernandez et al.

(10) Patent No.: US 7,800,379 B2
(45) Date of Patent: Sep. 21, 2010

(54) FUEL SENSOR

(75) Inventors: Norberto Hernandez, Chihuahua (MX);
Jesus Carmona, Columbus, IN (US);
Esau Aguinaga, Chihuahua (MX);
Manuel S. Sanchez, Chihuahua (MX);
Cecilia Hernandez, Chihuahua (MX);
Daniel J. Moreno, El Paso, TX (US);
Mark Shost, Northville, MI (US)

(73) Assignee: Delphi Technologies, Inc., Troy, MI (US)

( * ) Notice: Subject to any disclaimer, the term of this patent is extended or adjusted under 35 U.S.C. 154(b) by 99 days.

(21) Appl. No.: 12/326,332

(22) Filed: Dec. 2, 2008

(65) Prior Publication Data

US 2009/0153154 A1     Jun. 18, 2009

Related U.S. Application Data

(63) Continuation-in-part of application No. 11/954,824, filed on Dec. 12, 2007.

(51) Int. Cl.
*G01R 27/26* (2006.01)

(52) U.S. Cl. ..................... 324/663; 324/698

(58) Field of Classification Search .............. 324/663, 324/658, 649, 600, 698, 694, 693, 689, 686, 324/717, 76.11
See application file for complete search history.

(56) References Cited

U.S. PATENT DOCUMENTS

| | | | |
|---|---|---|---|
| 4,159,304 A | 6/1979 | Shono | |
| 5,101,367 A * | 3/1992 | Agar | 702/22 |
| 5,231,358 A | 7/1993 | Kapsokavathis et al. | |
| 5,315,159 A | 5/1994 | Gribnau et al. | |
| 5,570,030 A * | 10/1996 | Wightman | 324/694 |
| 5,995,888 A | 11/1999 | Hagenbuch et al. | |
| 6,125,696 A | 10/2000 | Hannan et al. | |
| 6,377,052 B1 * | 4/2002 | McGinnis et al. | 324/446 |
| 6,693,444 B2 | 2/2004 | Lin et al. | |
| 6,771,074 B2 * | 8/2004 | Zou et al. | 324/446 |
| 6,791,334 B2 * | 9/2004 | Horie et al. | 324/438 |
| 6,826,950 B2 | 12/2004 | Lecea et al. | |
| 6,836,123 B1 | 12/2004 | Qi et al. | |
| 6,927,583 B2 * | 8/2005 | Vanzuilen et al. | 324/686 |
| 6,965,243 B2 * | 11/2005 | Yamagishi et al. | 324/658 |
| 7,030,629 B1 * | 4/2006 | Stahlmann et al. | 324/663 |

(Continued)

OTHER PUBLICATIONS

PCT International Search Report dated Feb. 10, 2009.

*Primary Examiner*—Hoai-An D Nguyen
(74) *Attorney, Agent, or Firm*—Thomas N. Twomey (57) ABSTRACT

A sensing apparatus for determining a property of a fuel such as a gasoline and ethanol blend known as flex fuel includes an acetal plastic tube with an inlet, an outlet and a fuel passage in between. One property of the fuel is a dielectric constant. A pair of sensing plates are placed on opposite sides of the tube leaving the fuel passage unobstructed. A processing circuit on a printed circuit board (PCB) is located near to and is connected with the sensing plates. The circuit applies an excitation signal, senses a capacitance, and generates an output signal indicative of a property of the fuel. The sensed capacitance will increase with increasing concentration of ethanol in the fuel flowing through the passage. A shield for reducing EMI surrounds and encloses the sensing plates and the PCB. An interface connector allows the sensing apparatus to output the capacitance indicative signal to an engine controller or the like.

26 Claims, 8 Drawing Sheets

U.S. PATENT DOCUMENTS

| | | | |
|---|---|---|---|
| 7,135,870 B2 * | 11/2006 | Mohajer et al. | 324/639 |
| 7,183,778 B2 * | 2/2007 | Homan et al. | 324/693 |
| 7,361,065 B1 * | 4/2008 | Hardy et al. | 439/856 |
| 7,466,147 B2 * | 12/2008 | Stahlmann | 324/663 |
| 7,492,167 B2 * | 2/2009 | Reich et al. | 324/663 |
| 2002/0125899 A1 * | 9/2002 | Lvovich et al. | 324/698 |
| 2004/0043479 A1 * | 3/2004 | Briscoe et al. | 435/288.5 |
| 2005/0040576 A1 | 2/2005 | Oxenknech et al. | |
| 2005/0248358 A1 * | 11/2005 | Boyle et al. | 324/698 |
| 2006/0000445 A1 | 1/2006 | Iwaoka et al. | |
| 2006/0103393 A1 * | 5/2006 | Stahlmann et al. | 324/658 |
| 2006/0114007 A1 * | 6/2006 | Cho | 324/698 |
| 2006/0267600 A1 * | 11/2006 | Beatty | 324/698 |

* cited by examiner

FUEL SENSOR

CROSS-REFERENCE TO RELATED APPLICATIONS

This is a continuation-in-part (CIP) application of U.S. application Ser. No. 11/954,824 filed Dec. 12, 2007 entitled "OBSTRUCTIONLESS INLINE FLEX FUEL SENSOR", now pending, the disclosure of which is hereby incorporated by reference herein in its entirety.

TECHNICAL FIELD

The present invention relates generally to sensors and more particularly to a fuel sensor having sensing plates that do not obstruct a fuel passage.

BACKGROUND OF THE INVENTION

Due to the fact that ethanol is a renewable fuel, and for other reasons as well, the use of ethanol and ethanol blends (i.e., ethanol and gasoline) continues to grow. For example, flexible fuel vehicles are known that are designed to run on gasoline as a fuel or a blend of up to 85% ethanol (E85). Properties of such fuels, such as its conductivity or dielectric constant, can be used to determine the concentration of ethanol (or other alternate fuel) in the gasoline/alternate fuel blend and can also be used to determine the amount of water mixed in with the fuel. Experimental data shows that the fuel dielectric constant is directly proportional to the ethanol concentration but relatively insensitive to water contamination, provided that the water concentration is below about 1% since the dielectric constant of water is around 80 at 25° C. (i.e., surveys show that the water concentration on most U.S. Flex fuel stations is below 1%). On the other hand, fuel conductivity is very sensitive to water concentration. For example, ethanol has a dielectric constant of around 24 at 25 degrees Celsius while gasoline has a dielectric constant of around 2 at the same temperature. Determining the properties of such fuels is important for operation of a motor vehicle since an engine controller or the like can use the information regarding the composition, quality, temperature and other properties of the fuel to adjust air/fuel ratio, ignition timing and injection timing, among other things. Additionally, increasingly strict emissions-compliance requirements have only further strengthened the need for an accurate flexible fuel sensor.

As added background, most sensor technologies for fuel property sensing require in-situ signal processing electronics to convert the relatively small sensing signals to a suitably strong electrical signal that can be used by an external circuit, such as an engine controller, to define the measured fuel property of interest. For example only, a capacitive sensor, which is configured to apply an excitation signal to spaced apart sensing plates, induces a relatively small response signal, thus requiring local electronics to preserve the signal-to-noise ratio.

It is also known that most in-situ sensors (e.g., capacitive, inductive or magnetic technologies) do not require direct contact or exposure to the fuel in order to assess the relevant fuel properties. Nonetheless, these sensors generally benefit from the physical isolation from the fuel, since contact with the fuel can often degrade the performance of the sensor. While it is known to use coatings to isolate various sensor components from contact with the fuel, such coatings may induce stress and/or degrade the signal-to-noise ratio of the sensing approach.

Fuel passage obstruction is another shortcoming of conventional fuel sensors, particularly capacitance-based approaches. More specifically, to measure the capacitance of the fuel, conventional sensors are known to use plates with different shapes, but in all such applications these plates are inside the fuel line (i.e., the fuel passage). This makes the construction of such sensors more complex and poses a potential for obstructing the fuel flow. Additionally, this approach imposes stricter requirements to protect the plates from corrosion by the ethanol, as described above.

There is therefore a need for a fuel sensor that minimizes or eliminates one or more of the problems set forth above.

SUMMARY OF THE INVENTION

The invention is directed to a fuel sensing apparatus where the sensing plates are placed outside the fuel passage so that no obstruction to fuel flow is produced. Additionally, the sensing plates and signal processing electronics are located away from any contact with the fuel, reducing the risk of degradation due to corrosion, without the use of any coatings or the like, which simplifies the design.

An apparatus is provided for use in sensing one or more properties of a fuel. The apparatus includes a tube and first and second sensing plates. The tube extends along a longitudinal axis and has a hollow interior defining a fuel passage between a fuel inlet and a fuel outlet of the tube. The sensing plates are disposed outwardly of the tube, leaving the fuel passage unobstructed between inlet and outlet, and also isolating the plates from contact with the fuel. The tube may comprise material resistant to fuel, such as acetal thermoplastic material.

In a first embodiment, the sensing plates include a plurality of apertures configured to cooperate with a corresponding plurality of protuberances projecting from the tube to align and retain the sensing plates to the tube. A pair of spacer wheels, enlarged in diameter relative to the tube, extend radially outwardly from the tube at axially opposing ends. A generally cylindrical, hollow shield is located radially outwardly of the tube and is sized to engage and fit on the spacer wheels, where the shield and the spacer wheels cooperate to form a cavity. The cavity encloses the sensing plates and is configured in size and shape so as to be able to house a processing circuit on a printed circuit board (PCB). The processing circuit is therefore located near to and is electrically coupled with the sensing plates and is arranged to determine a characteristic (e.g., a capacitance) of the structure between the plates, which is mainly, in this embodiment, determined by the concentration of ethanol in the fuel flowing through the passage. The processing circuit is configured to generate an output signal indicative of one or properties of the fuel (e.g., dielectric constant).

Second and third embodiments include a tube assembly that is configured to include, among other things, a pair of laterally-disposed side pockets configured to receive and retain the sensing plates on opposing sides of the tube. The second embodiment includes a U-shaped holder that is configured to retain the internal components and to receive potting material to protect the internal components from environmental influences. The third embodiment also includes a holder, but which has a stepped configuration rather than a simpler U-shape, but likewise is also configured to accept potting material to protect the internal components. The second and third embodiments provide improved flexibility, including the configuration of an external housing and its mounting arrangement, to match the packaging requirements of a wide variety of applications.

Other features, aspects and advantages are presented.

BRIEF DESCRIPTION OF THE DRAWINGS

The present invention will now be described by way of example, with reference to the accompanying drawings.

DETAILED DESCRIPTION OF THE PREFERRED EMBODIMENT

Figure 1:
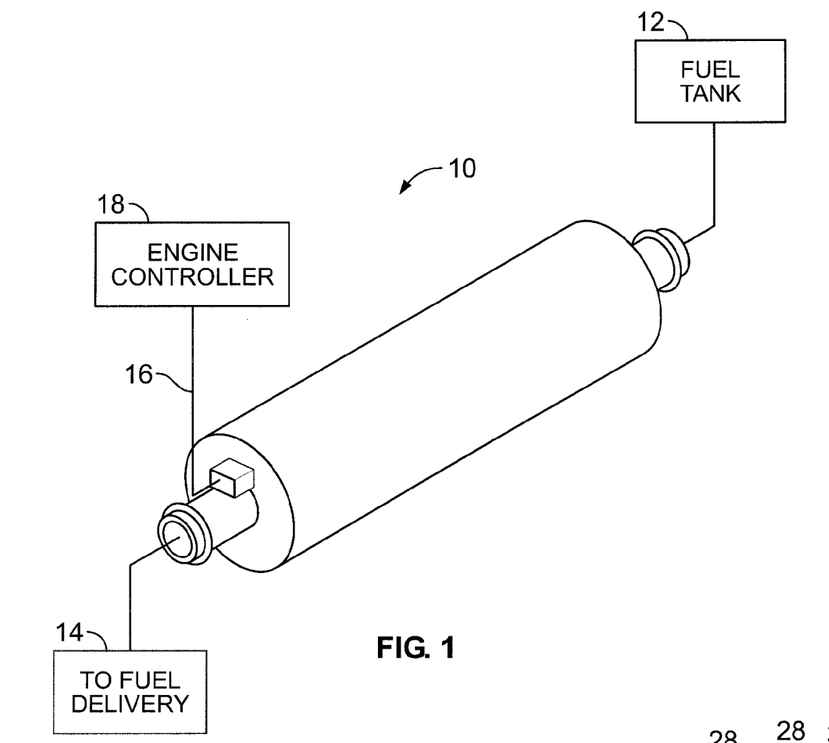
FIG. 1 is a top, perspective view of an embodiment of an obstructionless in-line flexible fuel sensing apparatus according to the invention.

Referring now to the drawings wherein like reference numerals are used to identify identical components in the various views, FIG. 1 is a perspective view of an apparatus 10 for sensing one or more properties of a fuel, such as a dielectric constant of a gasoline/ethanol blend. The sensing apparatus 10, as shown, is an in-line type fuel sensing apparatus that is coupled between a source of fuel, such as a fuel tank 12, and a destination, such as various fuel delivery apparatus 14 associated with an automotive vehicle internal combustion engine (not shown). The sensing apparatus 10, generally, includes a pair of sensing plates surrounding an inner tube, in a concentric manner, which are connected to a closely-located electrical circuit with signal processing capability so as to generate an output signal 16. The sensing plates around the inner tube will form a capacitor. The material between the plates includes a fixed portion, namely the tube walls, which have a fixed dielectric constant. However, the dielectric constant of the fuel flowing through the fuel line will vary, depending on the composition of the fuel itself. The total effective capacitance will be mainly driven by the variable portion. The circuit will measure the capacitance for purposes of generating the signal 16. The output signal 16 is indicative of one or more sensed physical properties of the fuel, such as dielectric constant or conductivity. In one embodiment, the output signal 16 may comprise a pulse-width modulated (PWM) signal indicative of an ethanol concentration level in the fuel of between about 0-100%. The output signal 16 may then be provided to, for example only, an electronic engine controller 18 or the like for use in, as known in the art, and as described in the Background, fuel delivery control.

Figure 2:
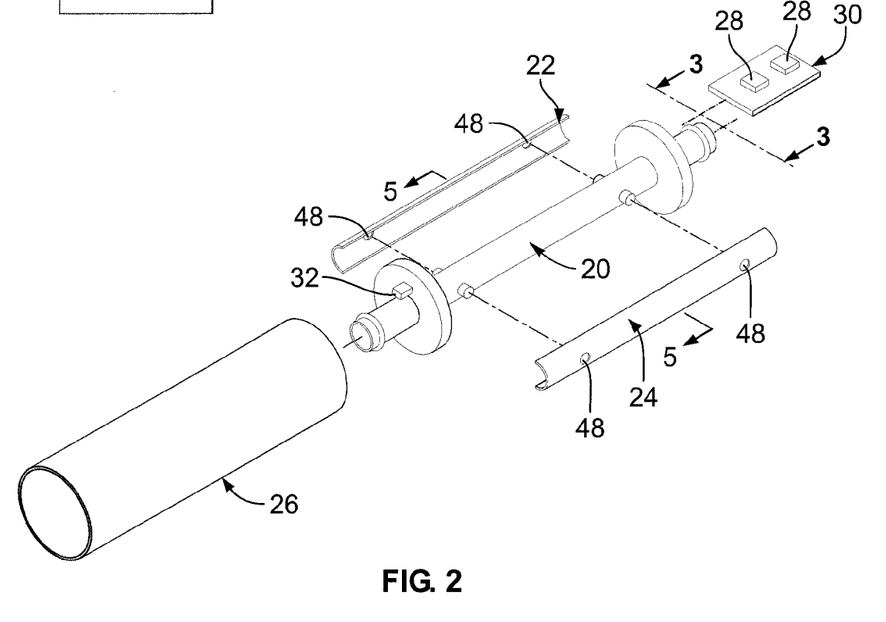
FIG. 2 is an exploded view of the fuel sensing apparatus of FIG. 1.

FIG. 2 is an exploded view showing in greater detail the sensing apparatus 10 and its constituent parts described generally above. The sensing apparatus 10 includes a tube 20, a first sensing plate 22, a second sensing plate 24, a shield 26, an electrical processing circuit 28 on a printed circuit board (PCB) 30 and an electrical connector 32. The stack-up assembly, as will be described, is generally concentric, starting with the tube 20 as the innermost component, then the plates 22, 24, and then the shield 26.

Figure 3:
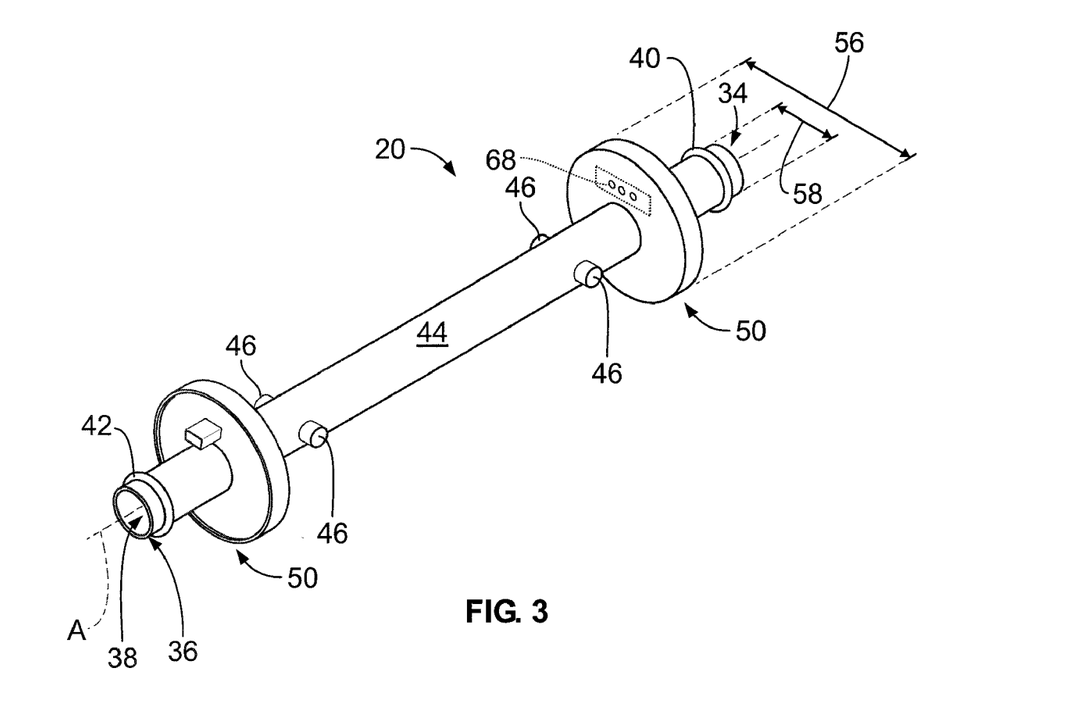
FIG. 3 is a perspective of a tube portion of the fuel sensing apparatus of FIG. 1 as viewed in the direction of line 3-3 in FIG. 2.

FIG. 3 is an enlarged perspective view showing the tube 20 in greater detail. The tube 20 extends along a main, longitudinal axis labeled "A". The tube 20 is preferably unitary (i.e., one piece) in construction, solid and continuous, and comprises plastic or other material that is resistant to degradation in the presence of various fuels including gasoline/ethanol blends. In one embodiment, the tube 20 is formed using an engineering plastic, such as a thermoplastic material known as acetal (or sometimes polyacetal). Acetal material exhibits desired chemical resistance properties with respect to the fuel that is contemplated to flow through the sensing apparatus 10.

As shown, the tube 20 includes an inlet 34, an outlet 36 and a fuel passage 38 (also shown in FIG. 5) formed in between. It should be appreciated that the inlet and outlet designations here are arbitrary, the principal of operation being applicable to fuel flows in either direction through the fuel passage 38. The inlet 34 and the outlet 36 each include a respective interface that is suitable for connection to a fuel hose or tube or other mechanism, as per the requirements of any particular application. For example only, as illustrated, the inlet 34 and the outlet 36 each include respective 0-ring seals 40, 42. Of course, other variations are possible. Significantly, the fuel passage 38 is unobstructed between the inlet 34 and the outlet 36. The sensing plates 22 and 24 are located outside of the tube 20 and hence out of the fuel passage 38, which is unlike the construction of conventional fuel sensors.

The tube 20 further includes an outer surface 44 spaced from the fuel passage 38 (i.e., by the wall thickness of the tube). The tube 20 is substantially circular in radial cross-section (best shown in FIG. 5). The tube 20 also includes a plurality of protuberances 46 configured to cooperate with a corresponding plurality of apertures 48 (FIG. 2) in the sensing plates 22 and 24 configured to align and retain the sensing plates 22, 24 with respect to the tube 20. The protuberances 46 may be snaps or heat stakes, or other conventional approaches for forming projections.

The tube 20 also includes a pair of spacer wheels 50 disposed on axially opposing ends 52 and 54 of the tube 20. Each spacer wheel 50 has a first outside diameter 56 that is larger than an outside diameter 58 of the tube 20. The spacer wheels 50 generally are configured to accommodate the shield 26 and form a fully enclosed sensing apparatus 10. It is preferred that the tube 20 as inclusive of the spacer wheels 50 be unitary (one-piece molded). The spacer wheels 50 may be formed with a radially-outermost sleeve, which if an outer edge is crimped, may be useful to hold the shield 26 in place.

Referring again to FIG. 2, the sensing plates 22 and 24 are generally semi-circular in shape and sized so as to snugly fit radially outwardly directly on the tube 20. The sensing plates 22 and 24 are preferably formed of an electrically-conductive material to which a copper wire or other conductor can be electrically-connected to (e.g., soldered), such as various thin plated metals and alloys known in the art for constructing sensing plates. For example, typical embodiments of the present invention may use a copper-based alloy (e.g., brass) for the sensing plates. The apertures 48 in the plates 22, 24 sized and located in correspondence with protuberances 46 so as to facilitate assembly of the plates to the tube 20. Upon assembly, the sensing plates 22 and 24 engage the outer surface 44 of the tube 20 wherein the sensing plates 22 and 24 and the tube 20 are in a concentric relationship with each other. This is best shown in FIG. 5.

The shield 26 is configured to reduce electromagnetic interference (EMI). More specifically, one function performed by the shield 26 is to minimize or eliminate the effect that stray or external electromagnetic interference may otherwise have on the sensing plates 22 and 24. A second function performed by the shield 26 is to minimize or eliminate any electromagnetic emissions produced by the excitation of the sensing plates 22 and 24 from propagating outwards from the sensing apparatus 10. As to construction, the shield 26 may comprise electrically-conductive material such as various metals and be coupled to a ground terminal of the interface connector 32, either directly via internal conductors or indirectly via a connection on the PCB 30. In the illustrated embodiment, the shield 26 is generally disposed radially outwardly of the tube 20, circumferentially continuous, and has an axial length sufficient to span the spacer wheels 50. The shield 26 is hollow and has an interior surface configured to engage and fit on the outside diameter of the spacer wheels 50. The shield 26 and the spacer wheels 50 cooperate to enclose the sensing plates 22 and 24. In addition, the shield 26 and the spacer wheels 50 cooperate to form a closed cavity 60 (i.e., the radially-outwardly extending space between the sensing plates/tube, on the one hand, and the interior surface of the shield 26, on the other hand.

Figure 5:
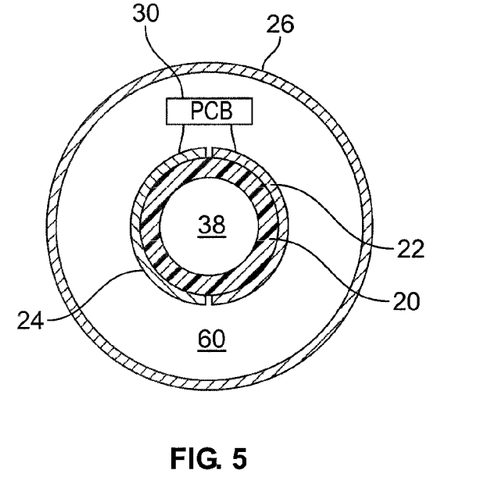
FIG. 5 is a cross-sectional view of a concentric tube and sensing plate assembly taken substantially along line 5-5 in FIG. 2.

FIG. 5 is a cross-sectional view of the sensing apparatus 10 taken substantially along line 5-5 in FIG. 2. As shown, the circuit 28 on the PCB 30 is electrically coupled to the sensing plates 22 and 24. Such a connection may be made using, conventionally, either separate wires or through suitably configured extensions of the sensing plates themselves that would terminate directly on the PCB. The PCB 30 is preferably located close to the sensing plates 22 and 24, and in the preferred embodiment, the PCB 30 is disposed within the cavity 60 of the sensing apparatus 10. The cavity 60 is thus configured in size and shape to at least house the printed circuit board (PCB) 30. While this will be described in greater detail below, generally, to perform its function, the signal processing circuit 28 is configured to apply suitable excitation signals to the sensing plates 22 and 24 and to detect and process the resulting induced signals to develop the output signal 16 indicative of a physical property of the fuel. The close proximity of the circuit 28 to the sensing plates improves the signal-to-noise ratio of the detected induced signal.

Figure 4:
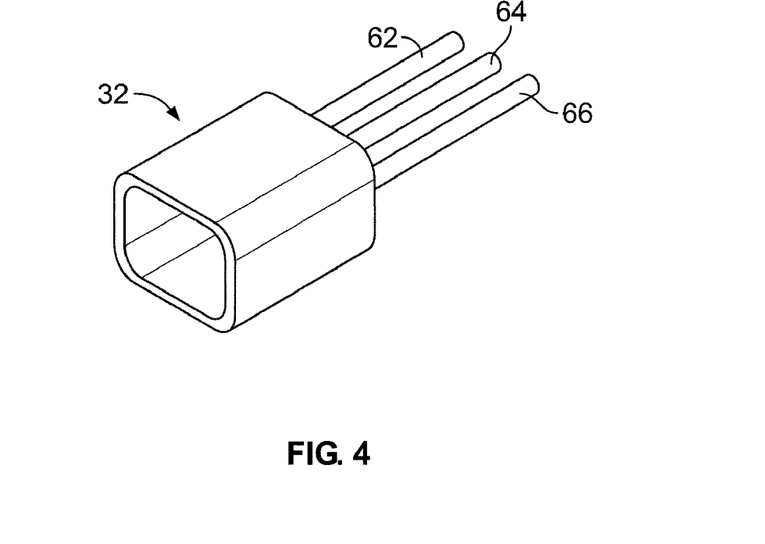
FIG. 4 is a perspective view of a connector portion of the fuel sensing apparatus of FIG. 2.

Referring to FIGS. 2 and 4, the interface connector 32 may comprise conventional construction approaches and materials, and may include a plurality of electrical terminals. In one embodiment, the connector 32 may include power, ground and output signal electrical terminals designated by reference numerals 62, 64 and 66, respectively (FIG. 4). Leads from these terminals 62, 64 and 66 are electrically connected to the circuit 28 on the PCB 30. In the embodiment where the PCB 30 is situated in the cavity 60, the leads 62, 64 and 66 from the connector 32 may pass through a series of axially-extending apertures 68 located in a main wall of one of the spacer wheels 50, as shown in FIG. 3 enclosed in a dashed-line box. The leads may then be connected to the PCB 30 using conventional means (e.g., soldering).

Figure 6:
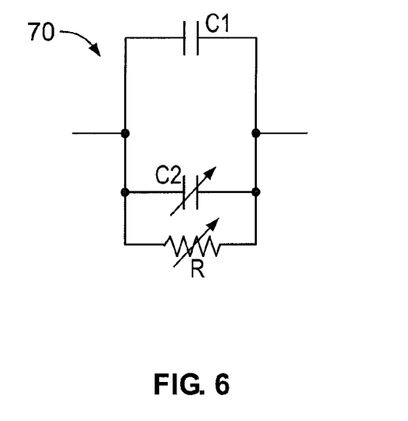
FIG. 6 is a simplified schematic diagram showing the fixed and variable capacitive contributions provided by the tube, and variable ethanol concentration fuel, respectively.

FIG. 6 is a simplified schematic diagram showing a simplified equivalent circuit 70 representing the sensing apparatus 10. It should be understood that in the present disclosure, a pair of sensing plates 22 and 24, with fuel flowing in the fuel passage 38, will appear to the electronics on PCB 30 as a complex load (e.g., a parallel combination of a resistor and a capacitor). More specifically, the tube 20 and the two sensing plates form a relatively small value capacitor, which is designated C1 in FIG. 5. Generally speaking, the value of C1 is fixed. When fuel flows through the fuel passage 38, an additional capacitance is added to the complex load, which is variable and depends on the particular properties of the fuel. This variable capacitance is designated C2 in FIG. 5. As described, the greater the ethanol concentration, the greater is the composite dielectric constant of the fuel blend. Since capacitance is determined based generally on plate geometry, spacing (which are fixed), and the dielectric constant of the material between the plates (which may vary here), it can be seen that the sensed capacitance C2 increases with higher concentrations of ethanol in a gasoline/ethanol blend. There is an additional resistive component, which is also variable, and is designated R in FIG. 5. This complex impedance comprises a real component part (resistive) and an imaginary component part (capacitive), which can be deconstructed and correlated to a conductivity and a dielectric constant, useful physical properties of the fuel. In particular, a dielectric constant can be derived from sensed capacitance using known relationships. The art is replete with approaches for measuring the complex impedance, or components thereof, for purposes of ascertaining one or more physical properties of the fuel, for example, as seen by reference to U.S. application Ser. No. 10/199,651 filed Jul. 19, 2002, now U.S. Pat. No. 6,693,444 B2 entitled "CIRCUIT DESIGN FOR LIQUID PROPERTY SENSOR" issued Feb. 17, 2004 to Lin et al., owned by the common assignee of the present invention, and hereby incorporated by reference in its entirety herein.

Figure 7:
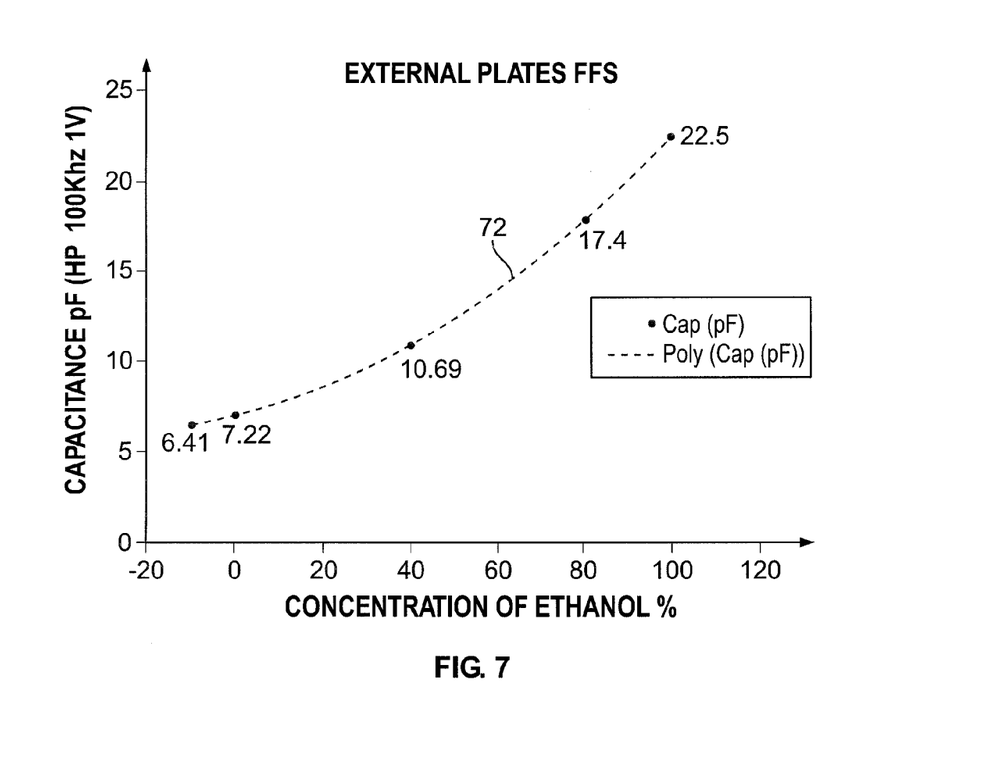
FIG. 7 is a diagram showing how the capacitance of a fuel flowing through the fuel sensing apparatus of FIG. 1 varies with ethanol concentration.

FIG. 7 is a chart showing the increase in sensed capacitance with increasing concentrations of ethanol in a gasoline/ethanol blend (e.g., a Flex Fuel). As shown, trace 72 represents a curve-fit relationship between particular measured plotted points. It should be understood that suitable a configuration of the signal processing circuit 28 may be employed to obtain a desired relationship of the output signal 16 and the variable concentration fuel. Alternatively, the controller 18 may be suitably configured to process a raw signal 16 to obtain or extract the desired information of the fuel properties.

Figure 8:
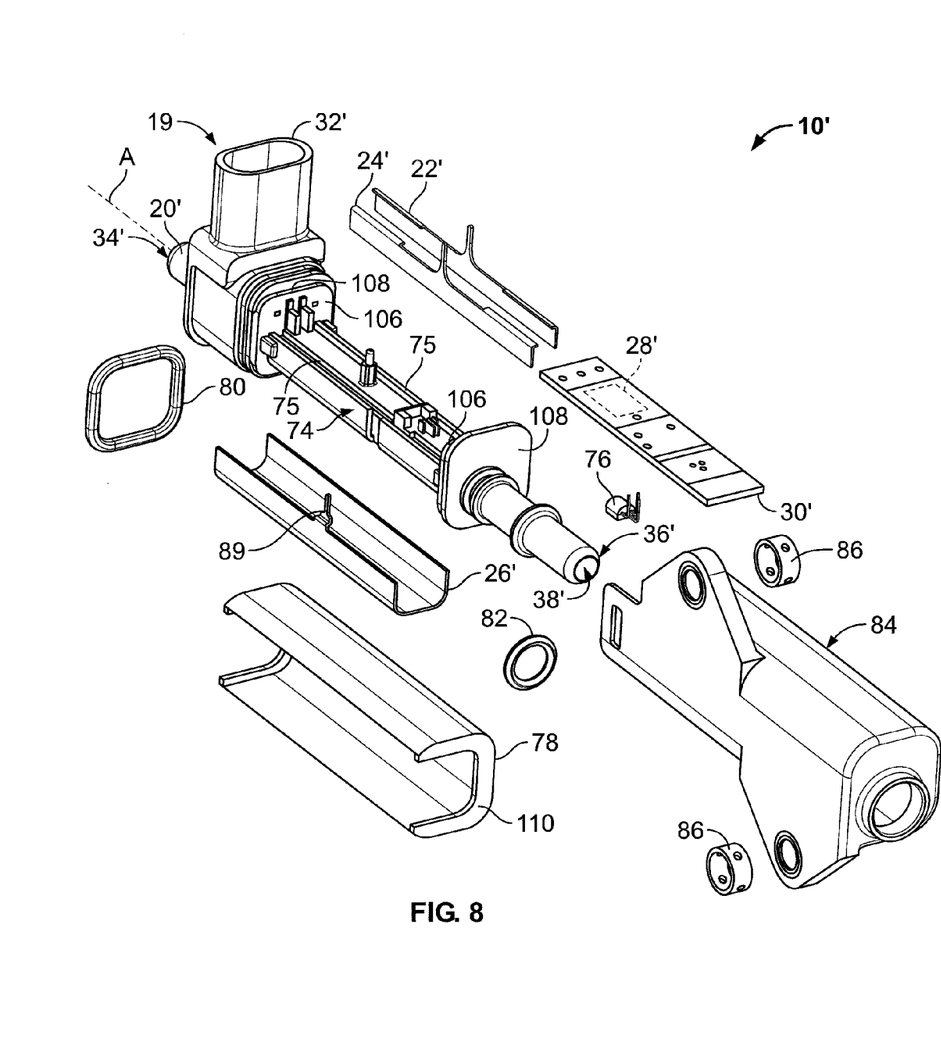
FIG. 8 is an exploded, perspective view of a second embodiment of a fuel sensing apparatus according to the invention.

FIG. 8 is an exploded, perspective view of a second embodiment of a fuel sensing apparatus, designated fuel sensing apparatus 10'. As with the first embodiment, the second embodiment simplifies the fuel impedance measurement by providing a structure that allows assembling of the sensing plates (electrodes) and signal processing electronics outside the tube through which the fuel flows. In the fuel sensing apparatus 10', since the tube material itself forms part of the sensing capacitor, the configuration allows for optimization and uniformity of the tube surface at or near this sensing location. In addition, the sensing apparatus 10' is modular in construction, which provides flexibility in changing the mounting configuration, fuel flow tube interface (i.e., at the inlet and outlet), electrical connector interface and electrical output signal configuration. In general, where the same or similar components are found in fuel sensing apparatus 10' as in the fuel sensing apparatus 10 the reference numerals are kept the same, except for the addition of a prime symbol (').

The sensing apparatus 10' is like the sensing apparatus 10, which as shown in FIG. 1, is an in-line type fuel sensing apparatus that is coupled between a source of fuel, such as a fuel tank 12, and a destination, such as various fuel delivery apparatus 14 associated with an automotive vehicle internal combustion engine (not shown). The sensing apparatus 10', generally, includes a pair of sensing plates on opposing sides of an inner tube, which are connected to a closely-located electrical circuit with signal processing capability so as to generate an output signal 16. The sensing plates on opposing sides of the inner tube will form a capacitor. The material between the plates includes a fixed portion, namely the tube walls, which have a fixed dielectric constant. However, the dielectric constant of the fuel flowing through the fuel line will vary, depending on the composition of the fuel itself. The total effective capacitance will be mainly driven by the variable portion. The circuit will measure the capacitance for purposes of generating the signal 16. The output signal 16 is indicative of one or more sensed physical properties of the fuel, such as dielectric constant or conductivity. The output signal 16 may then be provided to, for example only, an electronic engine controller 18 or the like for various uses described above.

With continued reference to FIG. 8, the fuel sensing apparatus 10 includes a tube assembly 19 having a central tube portion 20', sensing plates 22', 24', a shield 26', an electrical signal processing circuit 28' on a printed circuit board (PCB) 30' and an electrical connector 32'.

The tube assembly 19 extends along a main, longitudinal axis labeled "A". The tube assembly 19 may be unitary (i.e., one piece) in construction, solid and continuous, and comprises plastic or other material that is resistant to degradation in the presence of various fuels including gasoline/ethanol blends. The tube assembly 19 may be formed using an engineering plastic, such as a thermoplastic material known as acetal (or sometimes polyacetal). Acetal material exhibits desired chemical resistance properties with respect to the fuel that is contemplated to flow through the sensing apparatus 10'.

The tube 20' includes an inlet 34', an outlet 36' and a fuel passage 38' formed in between. It should be appreciated that the inlet and outlet designations here are arbitrary, the principal of operation being applicable to fuel flows in either direction through the fuel passage 38'. The inlet 34' and the outlet 36' each include a respective interface that is suitable for connection to a fuel hose or tube or other mechanism, as per the requirements of any particular application. Significantly, the fuel passage 38' is unobstructed between the inlet 34' and the outlet 36'. The sensing plates 22' and 24' are located outside of the tube 20' and hence out of the fuel passage 38', which is unlike the construction of conventional fuel sensors. The tube 20' further includes an outer surface spaced from the fuel passage 38' (i.e., by the wall thickness of the tube). The tube 20' may be substantially circular in radial cross-section.

The sensing plates 22', 24' are arranged to be located on opposing sides of the tube 20', and are configured to form "electrodes", with the material of the tube wall and the fuel in the passage 38' in between the "electrodes" in combination forming a "capacitor" whose capacitance is to be measured. From the measured capacitance, certain properties of the fuel, such as its dielectric constant, can be calculated, as described above.

The shield 26' is configured to reduce electromagnetic interference (EMI). More specifically, one function performed by the shield 26' is to minimize or eliminate the effect that stray or external electromagnetic interference may otherwise have on the sensing plates 22' and 24'. A second function performed by the shield 26' is to minimize or eliminate any electromagnetic emissions produced by the excitation of the sensing plates 22' and 24' from propagating outwards from the sensing apparatus 10'.

The circuit 28' includes various integrated circuit(s) and/or a microprocessor configured to excite the sensing plates, measure the resulting, induced signal and determine a complex impedance, and/or constituent real and imaginary components thereof, all as described above. The PCB 30' is configured to mechanically support the circuit 28' as well as provide an electrical interface with other, various components such as the sensing plates, the shield, the temperature sensor as well as the interface connector.

The interface connector 32' is configured to provide for electrical and mechanical connections between the sensing apparatus 10' and an engine control unit or the like. The connector 32' may comprise conventional construction approaches and materials, and may include a plurality of electrical terminals. In one embodiment, the connector 32' may include power, ground and output signal electrical terminals designated by reference numerals 62, 64 and 66, respectively (best shown in FIG. 4 for the sensing apparatus 10—this arrangement may be the same for sensing apparatus 10', although not specifically shown). Leads from these terminals are electrically connected to the circuit 28' on the PCB 30'.

The tube assembly 19 also includes a U-shaped channel member 74 having a base and a pair of legs extending from the base and configured to at least partially surround the tube 20'. The channel member 74 is further configured to have a width between the legs slightly greater than the tube diameter so as form a pair of electrode-receiving pockets 75 between the inside surfaces of the legs and the tube 20'. Each one of the pockets 75 is configured to receive a respective one of the sensing plates 22', 24'.

The sensing apparatus 10' further includes a temperature sensor 76, a holder 78, a pair of O-rings 80 and 82, and a housing 84 having one or more mounting holes formed therein including bushings 86.

The temperature sensor 76 is configured to detect the temperature of the fuel in the fuel passage 38' and generate a temperature indicative signal, which may be used by the circuit 28'. Specifically, the circuit 28' is configured to interact with the sensor 76 to accomplish the measurement of the fuel temperature, and may be configured to use the measured fuel temperature to make compensations in the calculated complex impedance (or constituent aspects thereof, or derivations there of, such as the dielectric constant of the fuel).

The holder 78 is configured to cooperate with the tube assembly 19 so as to form a cavity that is closed other than for an opening. The cavity (once formed after installation of the holder 78) may be used to hold potting material that protects and supports the electrical components and interfaces during the service life the sensing apparatus 10'. The holder 78 will be described in greater detail below.

The O-rings 80 and 82 are configured to cooperate with the housing 84 to seal off the interior from external environmental influences, such as water, dirt, humidity, etc.

The housing 84 is configured to provide the mechanical protection to the interior components of the sensing apparatus 10'. Further, the housing 84 includes a flexible mounting interface for securing the sensing apparatus 10' in a desired manner in any desired application. In the illustrative embodiment, the housing 84 includes a pair of mounting holes in which are installed respective bushings 86.

The sensing plates 22', 24', the shield 26 (or ground plate), the PCB 30', the temperature sensor 76, the holder 78 and the housing 84 are assembled over or around the tube assembly 19. As will be described in greater detail, these components are supported mechanically by a variety of features included in the tube assembly 19.

Figure 9:
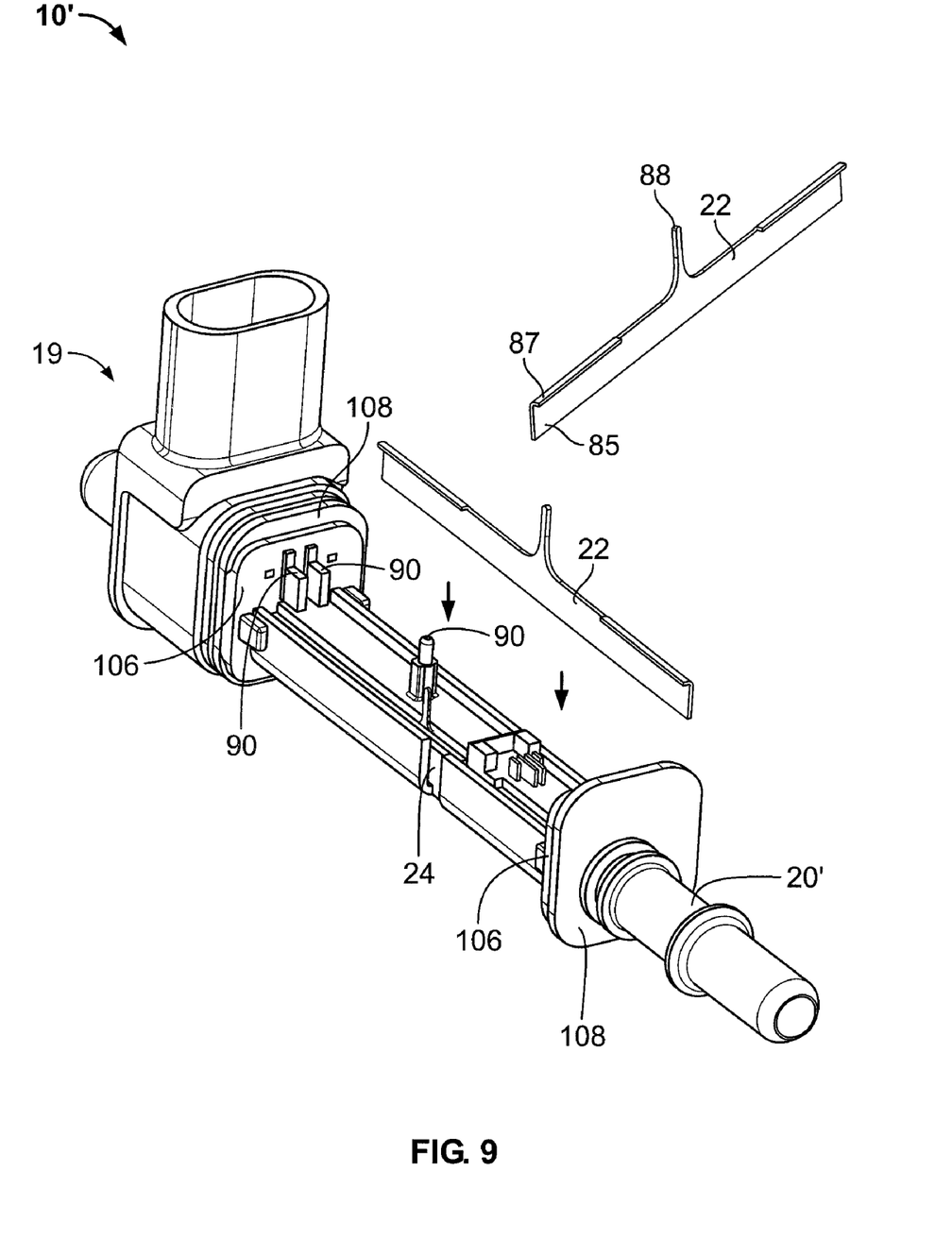
FIG. 9 is a perspective view of the fuel sensing apparatus of FIG. 8 showing the insertion phase of the assembly.

FIG. 9 is a perspective view of the fuel sensing apparatus 10' of FIG. 8. Each of the sensing plates 22' and 24' in this second embodiment have a main, planar body portion 85 and a distal portion 87 that is curved so as to generally approximate a J-shape overall. In addition, each sensing plate 22', 24' includes a respective projection 88 configured for electrical connection to the circuit 28' disposed and/or formed on the PCB 30'. The sensing plates 22' and 24' are preferably formed of an electrically-conductive material to which a copper wire or other conductor can be electrically-connected to (e.g., soldered), such as various thin plated metals and alloys known in the art for constructing sensing plates. For example, typical embodiments of the present invention may use a copper-based alloy (e.g., brass) for the sensing plates. To assemble, each sensing plate 22' and 24' is inserted from the top into its respective pocket 75, as shown.

The tube assembly 19 also includes a plurality of stand-offs 90 that are configured to receive and mount the PCB 30'. When mounted, the PCB 30' is positioned and aligned in a predetermined, desired manner relative to the tube 20'. In the illustrative embodiment, the stand-offs 90 are located at axially opposing ends of the channel member 74 as well as in at least one location in between. The stand-offs 90 may further include a shoulder or like mechanical arrangement so as to position the PCB 30' both radially with respect to the tube 20', as well as axially. These aspects of the positioning are particularly important insofar as holes in the PCB 30' must be in registry with various connections from the sensing plates 22', 24' (i.e., the projections 88), the shield 26' (i.e., the extension 89) and the temperature sensor 76 (i.e., the terminals 100-best described in connection with FIGS. 10-11 below).

Figure 10:
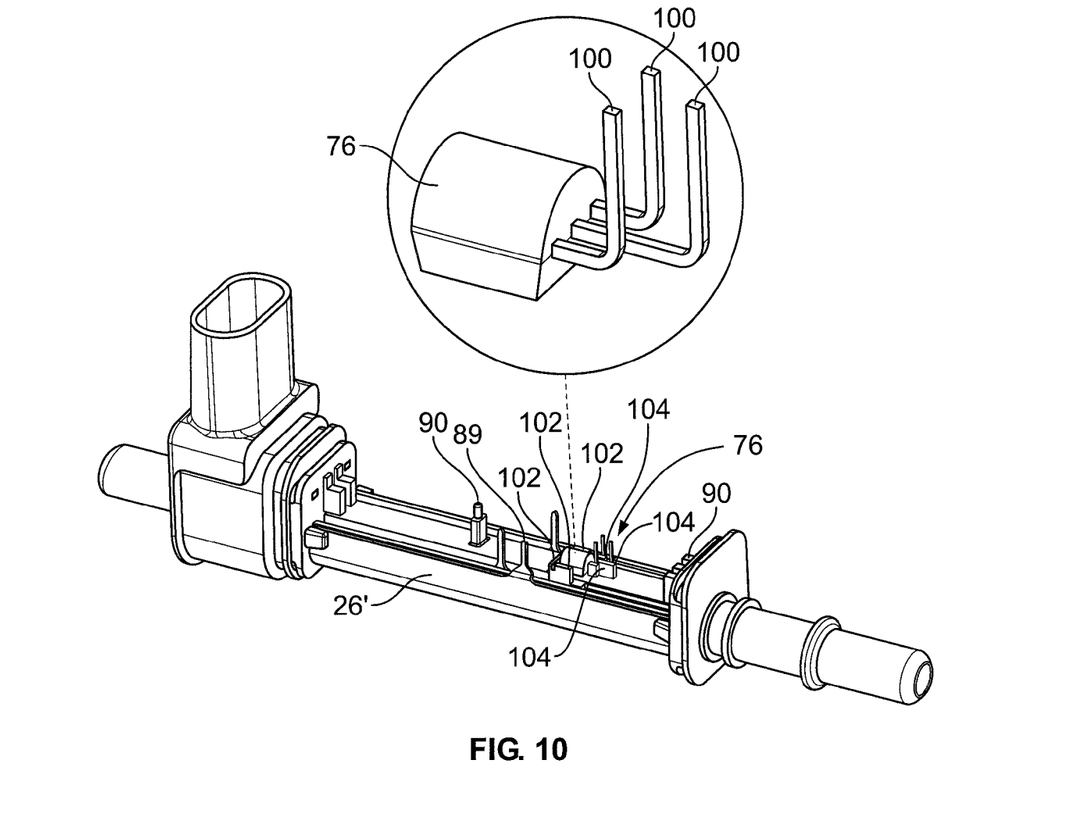
FIG. 10 is a perspective view showing further features of the tube assembly including features configured to receive and retain a fuel temperature sensor.

FIG. 10 is a perspective view showing further features of the sensing apparatus 10'. The shield 26' is shown assembled to the tube assembly 19, more specifically to the outer surface of the channel member 74. The shield 26' includes an extension 89 configured in size and shape for electrical connection to the circuit 28' disposed and/or formed on the PCB 30'. As to construction, the shield 26' may comprise electrically-conductive material such as various metals and be coupled to a ground terminal of the interface connector 32', preferably by way of a connection on the PCB 30'. In the illustrated embodiment, the shield 26' is generally U-shaped and is disposed outwardly of the channel member 74.

The temperature sensor 76 includes a plurality of connecting terminals 100. Mechanically, the tube assembly 19 includes a plurality of lands 102 projecting upwardly (i.e., radially outwardly relative to the tube 20') and arranged so as to form a well configured in size and shape to receive the temperature sensor 76. In addition, the tube assembly 19 further includes one or more supports 104, also projecting upwardly (i.e., radially outwardly relative to the tube 20') and configured in size and shape to abut and support the terminals 100, particularly when the PCB 30' is assembled onto the tube assembly 19. When inserted in the well, the temperature sensor 76 is disposed proximate the tube 20' and given this proximity is configured to generate a temperature signal that is fairly indicative of a temperature of the fuel in the passage 38'.

Figure 11:
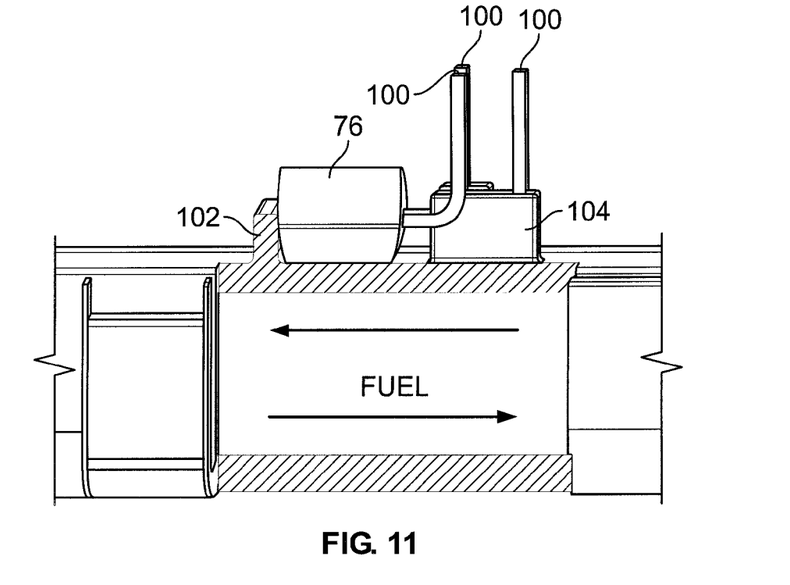
FIG. 11 is a partial, cross-sectional view showing, in greater detail, the temperature sensor receiving and retaining features of FIG. 10.

FIG. 11 is a partial, cross-sectional view showing, in greater detail, the temperature sensor 76 and its terminals 100, as well as the corresponding 102 and supports 104. As shown, the temperature sensor 76 is near enough to the fuel so as to produce a reasonably accurate indication of the fuel temperature. The terminals 100 are configured for electrical connection to the circuit 28'.

Figure 12:
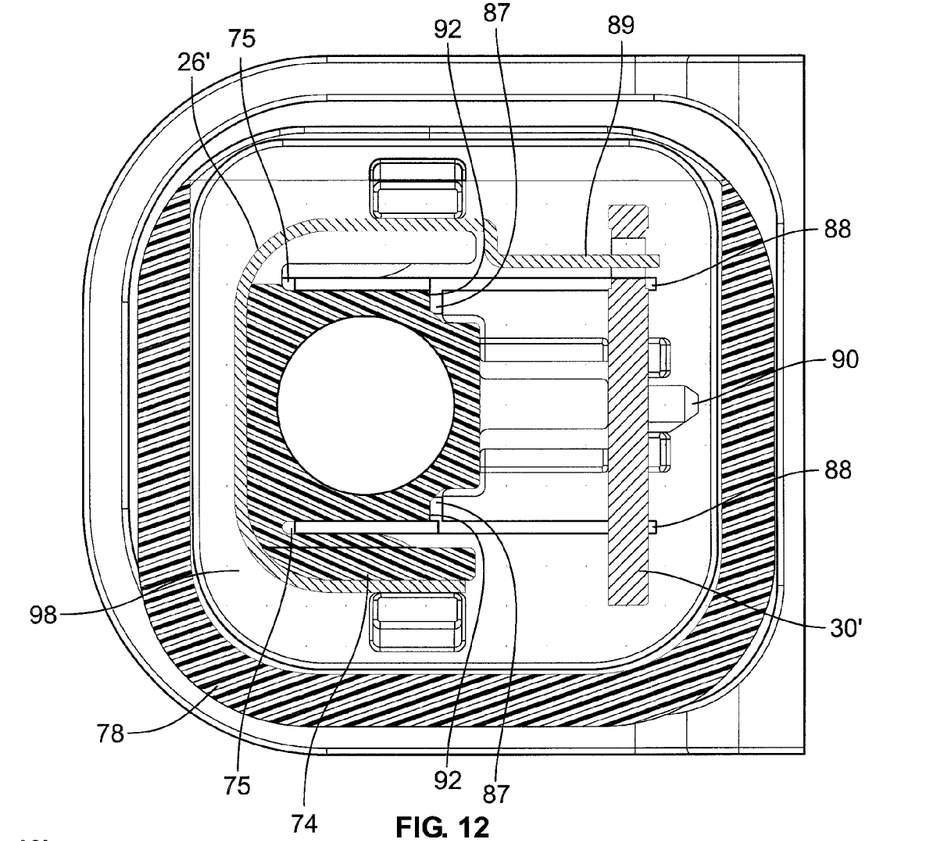
FIG. 12 is a cross-sectional view of a partially-assembled fuel sensing apparatus showing the stack-up of components.

FIG. 12 is a cross-sectional view of a partially-assembled fuel sensing apparatus 10'. There are a number of steps in the assembly. As shown, the sensing plates 22', 24' are inserted into their respective pockets 75 (best shown FIG. 9). The distal portion 87 of the plates abuts a lip or ledge 92. Then, the shield 26' is slid or snapped on the outside of the channel member 74 (best shown in FIG. 10). Also, the temperature sensor 76 is disposed in its well, in accordance with the orientation best shown in FIG. 11. After these steps, the PCB 30' is installed. Specifically, as shown, the PCB 30' is positioned, through the assistance of the stand-offs 90, so that a number of holes in the PCB 30' are in registry with corresponding electrical connectors so as to allow a direct electrical connection to the sensing plates 22', 24' (i.e., by way of the projections 88 to the PCB 30'), the shield 26' (i.e., by way of the extension 89 to the PCB 30') and the temperature sensor 76 (i.e., by way of the terminals 100 to the PCB 30'). Conventional approaches may be used (e.g., soldering) to make these electrical connections once the PCT 30' is in place and these items are in their connecting holes.

After these steps, the holder 78 is slid onto the tube assembly 19. As best shown in FIG. 8, the tube assembly 19 includes a pair of mounts 106, 108 at each axial end of the member 74 (i.e., axially offset along the tube 20'). In the embodiment of FIGS. 8-13, the holder 78 includes an end surface 110 (on both ends) that is configured to engage the surfaces of mounts 108 while the holder slides onto mounts 106. The holder 78 is thus configured to be received on the mounts 106 with the surfaces 110 engaging the surfaces of mounts 108. This forms an interior space with an opening, which in the orientation shown in FIG. 8 opens up facing the side. The interior space forms a holding volume that is configured in size and shape to contain the tube 20', the sensing plates 22' and 24', the temperature sensor 76, the channel member 74, the PCB 30' and the shield 26'. This sub-assembly is then rotated 90 degrees and the interior space is filled with potting material 98 through the opening up to a predetermined level, thereby encapsulating the interior components, as shown in FIG. 12.

Figure 13:
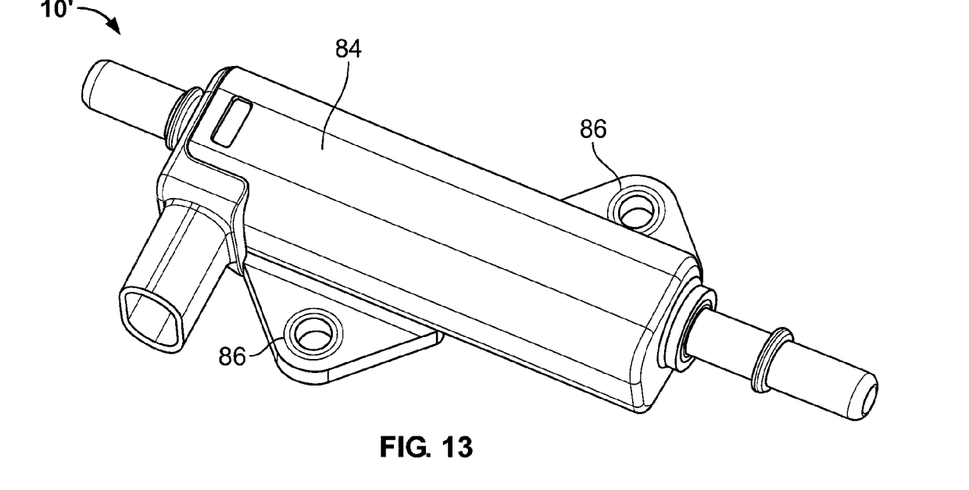
FIG. 13 is a perspective view of the fuel sensing apparatus of FIG. 8 as fully assembled.

FIG. 13 is a perspective view of the sensing apparatus 10' as fully assembled (i.e., after the housing 84 has been installed). Before the housing 84 is installed, however one or more O-ring seals 80 and 82 may be installed on the tube assembly 19. The O-ring seals 80, 82 are best shown in FIG. 8. The housing 84 is then slid axially onto and/or over the tube assembly 19 until it is fully seated, as shown.

The overall operation of apparatus 10' is the same as described above in connection with the sensing apparatus 10, including particularly the description given in connection with FIGS. 6 and 7. It should be understood that all that was described above in connection with apparatus 10 applies with equal force to the operation of the apparatus 10' unless otherwise indicated. Generally, to perform its function, the signal processing circuit 28' is configured to apply suitable excitation signals to the sensing plates 22' and 24' and to detect and process the resulting induced signals to develop the output signal 16. The output signal 16 is indicative of a physical property of the fuel. The close proximity of the circuit 28' to the sensing plates improves the signal-to-noise ratio of the detected induced signal.

Figure 14:
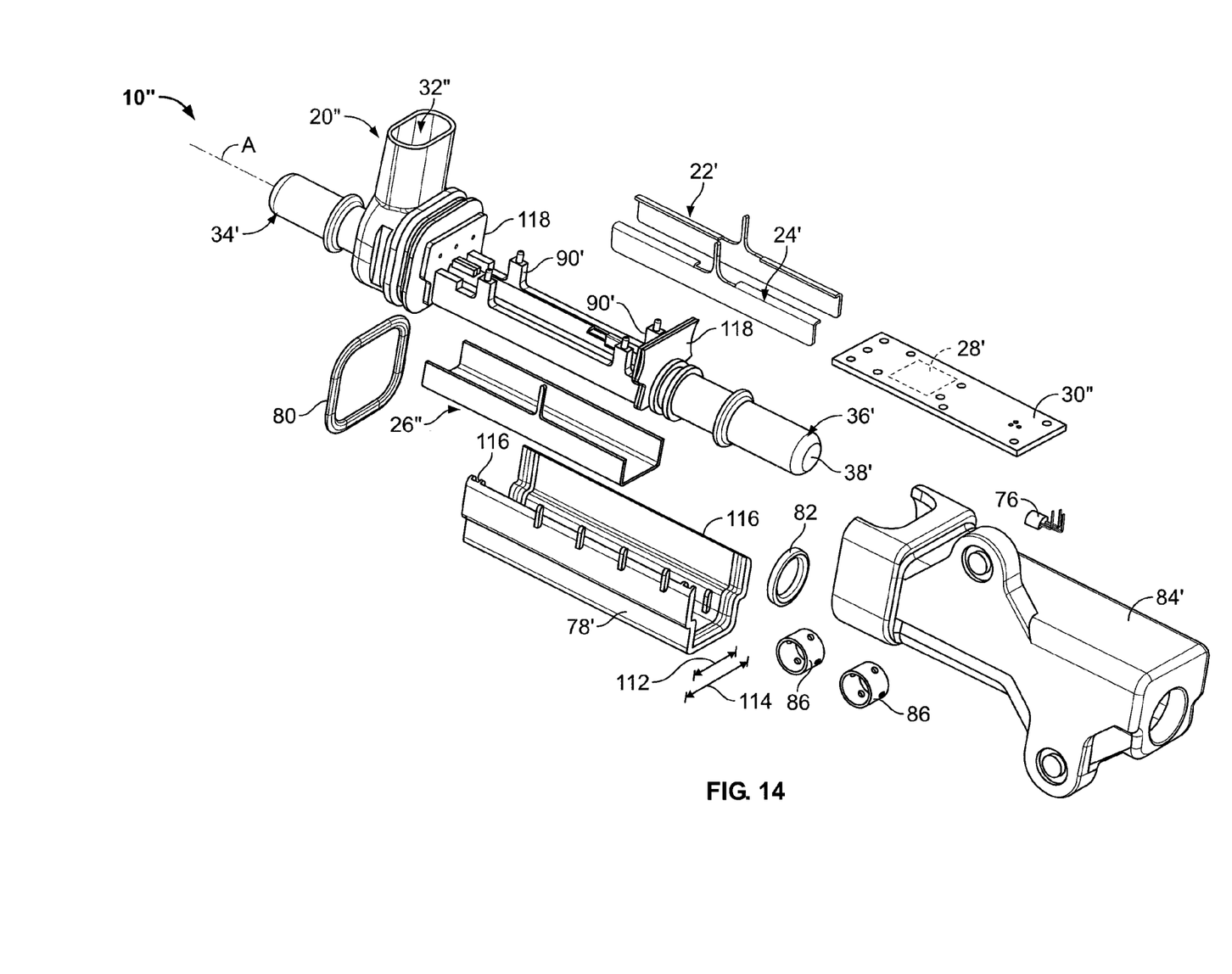
FIG. 14 is an exploded, perspective view of a third embodiment of a fuel sensing apparatus according to the invention.

FIG. 14 is an exploded, perspective view of a third embodiment of a fuel sensing apparatus 10" according to the invention. Apparatus 10" is substantially the same as apparatus 10', except as follows. The holder 78' is of a stepped configuration and is arranged to be assembled from the bottom of the tube assembly 19 so that its mouth or opening is already facing an "up" orientation (rather than having to be rotated 90 degrees as with the embodiment of FIGS. 8-13). The holder 78' has a floor, a first pair of sidewalls extending from the floor, and a second pair of sidewalls extending from the first pair of sidewalls. The interior of the holder 78' forms a stepped configuration. As shown, a lower U-shaped channel has a width designated 112, while an upper U-shaped channel has an enlarged width, designated 114. The holder 78' also includes a pair of slots 116 on axially opposing end and on an inside surface of the holder.

The tube assembly 19 of apparatus 10" is also varied insofar as the stand-offs 90 now extend from the side legs of the channel member 74 rather than from the top of the tube assembly 19. Also, the tube assembly 19 includes a pair of mounts 118 that are generally T-shaped in the illustrated embodiment. The slots 116 of the holder 78' are configured to fit on the mounts 118 wherein the mounts 118 post-assembly define a pair of end-walls closing the interior that is formed, other than for the "top" opening. In this embodiment, the member 74, the shield 26' and the holder 78' are in a nested relation, one to the other.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

The invention claimed is:

1. An apparatus for use in sensing one or more properties of a fuel, comprising:
    a tube extending along a longitudinal axis, said tube having a hollow interior defining a fuel passage between a fuel inlet and a fuel outlet;
    first and second sensing plates being disposed radially outwardly of said tube on an outer surface thereof so as to leave said fuel passage unobstructed, wherein said sensing plates comprise electrically-conductive material;
    an electrical circuit configured on a printed circuit board (PCB), said circuit being electrically coupled to said sensing plates and configured to generate an output signal indicative of the one or more properties of said fuel;
    a shield comprising electrically-conductive material configured to reduce electromagnetic interference (EMI); and
    a generally U-shaped channel member having a base and a pair of legs extending from said base and configured to received said tube, said channel member having a width between said legs so as to form a pair of pockets between inside surfaces of said legs and said tube, each pocket being configured to receive a respective one of said sensing plates.

2. The apparatus of claim 1 wherein said tube comprises electrically-insulating thermoplastic material.

3. The apparatus of claim 2 wherein said thermoplastic material comprises acetal material.

4. The apparatus of claim 1 further including a temperature sensor disposed proximate said tube configured to generate a temperature signal indicative of a temperature value of the fuel in said tube, said sensor being electrically connected to said circuit.

5. The apparatus of claim 1 wherein each of said sensing plates includes a respective projection configured for electrical connection to said circuit, said shield including an extension configured for electrical connection to said circuit.

6. The apparatus of claim 1 wherein one of said properties comprises a dielectric constant of the fuel flowing through said fuel passage.

7. The apparatus of claim 1 wherein at least a portion of an outside surface of said tube is circular, said sensing plates having a main, planar body portion and a distal portion that is curved so as to conform to the circular outside surface of said tube.

8. The apparatus of claim 1 wherein said shield is grounded.

9. The apparatus of claim 1 further including a connector comprising electrical terminals, said connector being coupled to said PCB.

10. The apparatus of claim 1 further including a pair of spacer wheels disposed on axially opposing ends of said tube, a first outside diameter of said spacer wheels being larger than a second outside diameter of said tube, said shield radially outwardly of said tube, said shield being hollow and having an interior surface configured to engage and fit on said spacer wheels, said shield and spacer wheels cooperating to enclose said sensing plates and form a closed cavity.

11. The apparatus of claim 10 wherein said PCB is located in said closed cavity.

12. The apparatus of claim 1 wherein said tube is substantially circular in radial cross-section, said sensing plates comprising electrically-conductive material and being semi-circular in shape, said sensing plates and said tube being in concentric relation.

13. The apparatus of claim 12 wherein said tube comprises a plurality of protuberances configured to cooperate with a corresponding plurality of apertures in said sensing plates configured to align and retain said sensing plates to said tube.

14. The apparatus of claim 1 further including a plurality of stand-offs wherein said PCB is configured to be mounted to said stand-offs so as to position and align said PCB relative to said tube.

15. The apparatus of claim 1 wherein said shield is generally U-shaped and disposed outwardly of said channel member.

16. The apparatus of claim 14 further including:
    a pair of mounts axially offset along the tube; and
    a holder configured to be received on said pair of mounts to thereby form an interior with an opening, said interior being configured in size and shape to contain said shield, said U-shaped channel member, said sensing plates, and a portion of said tube.

17. The apparatus of claim 16 further including a housing configured to enclose said holder.

18. The apparatus of claim 17 wherein said housing includes at least a mounting flange configured for securing said apparatus.

19. The apparatus of claim 16 wherein said holder has a floor wall, a first pair of sidewalls extending from said floor wall, and a second pair of sidewalls extending from said first pair of sidewalls wherein said interior is a stepped interior, said holder further including a pair of slots formed at axially opposing ends on an inside surface thereof, each of said slots being configured to receive one of said mounts wherein said mounts define a pair of end walls closing said interior other than for said opening, said U-shaped channel member, said shield and said holder being in a nested relation with each other.

20. The apparatus of claim 19 wherein said mounts are generally T-shaped.

21. The apparatus of claim 16 wherein said holder has a floor wall, and a first pair of sidewalls extending from said floor wall, said holder further including a pair of slots formed at axially opposing ends on an inside surface thereof, each of said slots being configured to receive one of said mounts wherein said mounts define a pair of end walls closing said interior other than for said opening.

22. The apparatus of claim 16 further including potting material in said interior of said holder to at least cover said PCB.

23. A fuel sensor comprising:
 a tube assembly comprising (i) a tube formed of thermoplastic material extending along a longitudinal axis, said tube having a hollow interior defining a fuel passage between a fuel inlet and a fuel outlet; (ii) a generally U-shaped channel member outwardly of said tube and defining a pair of pockets on each side of said tube; (iii) a pair of mounts; and (iv) an interface connector comprising an electrical terminal;
 a pair of sensing plates disposed in said pockets,
 a shield outwardly of said channel member that is grounded;
 a holder configured to be received on said mounts to thereby form an interior with an opening, said interior being configured in size and shape to contain said shield, said U-shaped channel member, said sensing plates, and a portion of said tube, said interior containing potting material;
 an electrical circuit on a printed circuit board (PCB) disposed in said interior, said circuit being electrically coupled to said sensing plates and configured to generate an output signal, coupled to said electrical terminal of said connector, indicative of one or more properties of said fuel; and
 a housing configured to enclosed said holder.

24. The apparatus of claim 23 wherein said circuit is configured to excite said sensing plates and detect the resulting induced signals, wherein one of said properties is a dielectric constant.

25. The apparatus of claim 23 wherein said thermoplastic material comprises acetal material.

26. The apparatus of claim 23 further including a temperature sensor disposed proximate said tube configured to generate a temperature signal indicative of a temperature value of the fuel in said tube, said sensor being electrically connected to said circuit.

* * * * *